United States Patent
Sanchez

(10) Patent No.: US 10,475,001 B1
(45) Date of Patent: *Nov. 12, 2019

(54) TECHNOLOGY FOR AUTOMATICALLY IDENTIFYING AND SCHEDULING PROVIDER APPOINTMENTS IN RESPONSE TO ACCIDENT EVENTS

(71) Applicant: STATE FARM MUTUAL AUTOMOBILE INSURANCE COMPANY, Bloomington, IL (US)

(72) Inventor: Kenneth J. Sanchez, San Francisco, CA (US)

(73) Assignee: STATE FARM MUTUAL AUTOMOBILE INSURANCE COMPANY, Bloomington, IL (US)

( * ) Notice: Subject to any disclaimer, the term of this patent is extended or adjusted under 35 U.S.C. 154(b) by 294 days.

This patent is subject to a terminal disclaimer.

(21) Appl. No.: 15/476,452

(22) Filed: Mar. 31, 2017

Related U.S. Application Data

(63) Continuation of application No. 15/180,784, filed on Jun. 13, 2016, now Pat. No. 9,652,748.

(51) Int. Cl.
*G06Q 10/10* (2012.01)
*B60R 21/00* (2006.01)

(52) U.S. Cl.
CPC ......... *G06Q 10/1095* (2013.01); *B60R 21/00* (2013.01); *B60R 2021/0027* (2013.01)

(58) Field of Classification Search
CPC .......................................... G06Q 10/00–50/00
USPC .............................................. 705/7.11–7.42
See application file for complete search history.

(56) References Cited

U.S. PATENT DOCUMENTS

| | | | | |
|---|---|---|---|---|
| 6,526,335 B1 * | 2/2003 | Treyz | ..................... | G01C 21/26 307/10.1 |
| 6,738,697 B2 * | 5/2004 | Breed | ..................... | B60C 11/24 701/31.5 |
| 7,103,460 B1 * | 9/2006 | Breed | ................. | B60C 23/0408 701/29.1 |
| 8,060,395 B1 * | 11/2011 | Frasher | .............. | G06Q 10/1093 705/7.18 |

(Continued)

OTHER PUBLICATIONS blog.allstate.com, "How to Avoid Buying a Car with a Safety Recall," (Apr. 10, 2013). Retrieved from the Internet on Aug. 11, 2014: http://blog.allstate.com/how-to-avoid-buying-a-car-with-a-safety-recall/.

(Continued)

*Primary Examiner* — Alan S Miller
(74) *Attorney, Agent, or Firm* — Marshall, Gerstein & Borun LLP; Randall G. Reuth

(57) ABSTRACT

Systems and methods for managing accident events are disclosed. According to certain aspects, an electronic device may access sensor data associated with operation of a vehicle, and analyze the sensor data to determine that an accident event has occurred, where the accident event may have one or more effects such as damage or injury. The electronic device may also interface with a server to identify one or more providers who may be capable of addressing the effects of the accident event. The electronic device or the server may automatically schedule an appointment(s) with the one or more providers, resulting in an effective handling of the accident event.

20 Claims, 5 Drawing Sheets

(56) References Cited

U.S. PATENT DOCUMENTS

| | | | |
|---|---|---|---|
| 8,335,616 B2* | 12/2012 | Neal | B60R 25/00 180/271 |
| 8,478,630 B2* | 7/2013 | Reichman | G06Q 10/06314 705/7.32 |
| 8,811,938 B2* | 8/2014 | Paek | H04W 4/90 455/404.2 |
| 9,082,239 B2* | 7/2015 | Ricci | B60Q 1/00 |
| 9,286,736 B2* | 3/2016 | Punjabi | G06Q 30/016 |
| 9,333,913 B1* | 5/2016 | Elders | B60Q 9/008 |
| 2002/0016655 A1* | 2/2002 | Joao | G07C 5/008 701/33.4 |
| 2002/0116103 A1* | 8/2002 | Matsunaga | G07C 5/008 701/32.7 |
| 2003/0107548 A1* | 6/2003 | Eun | G07C 5/008 345/156 |
| 2004/0022416 A1* | 2/2004 | Lemelson | G01S 13/931 382/104 |
| 2004/0153356 A1* | 8/2004 | Lockwood | G06Q 10/20 705/305 |
| 2004/0203974 A1 | 10/2004 | Seibel | |
| 2005/0037730 A1* | 2/2005 | Montague | B60R 25/1004 455/404.2 |
| 2005/0060067 A1 | 3/2005 | Nishida | |
| 2007/0093947 A1* | 4/2007 | Gould | G07C 5/008 701/31.5 |
| 2007/0100519 A1* | 5/2007 | Engel | G07C 5/008 701/31.4 |
| 2007/0179860 A1 | 8/2007 | Romero | |
| 2009/0106036 A1* | 4/2009 | Tamura | G06Q 10/109 705/305 |
| 2012/0004943 A1* | 1/2012 | Reichman | G06Q 10/06314 705/7.24 |
| 2012/0078472 A1* | 3/2012 | Neal | B60R 25/00 701/45 |
| 2012/0123611 A1 | 5/2012 | Grasso et al. | |
| 2014/0278674 A1* | 9/2014 | Gohar | G06Q 50/01 705/7.19 |
| 2015/0084757 A1* | 3/2015 | Annibale | G08B 25/10 340/436 |
| 2015/0302667 A1* | 10/2015 | Punjabi | G07C 5/008 701/31.4 |

OTHER PUBLICATIONS carfax.com, "Free Carfax Recall Check." Retrieved form the Internet on Aug. 11, 2014: http://www.carfax.com/recall_check.cfx.

progressive.com, "Vehicle Recall Search," (1995-2014). Retrieved from the Internet on Aug. 11, 2014: http://www.progressive.com/vehicle-resources/vehicle-recall-search/.

U.S. Appl. No. 14/451,059, Binion et al., "Systems and Methods for Managing and Communicating Vehicle Notifications for Various Circumstances", filed Aug. 4, 2014.

* cited by examiner

TECHNOLOGY FOR AUTOMATICALLY IDENTIFYING AND SCHEDULING PROVIDER APPOINTMENTS IN RESPONSE TO ACCIDENT EVENTS

CROSS-REFERENCE TO RELATED APPLICATIONS

The present application is a continuation of U.S. patent application Ser. No. 15/180,784, filed Jun. 13, 2016, the disclosure of which is hereby fully incorporated by reference in its entirety.

FIELD

The present disclosure is directed to managing accident events involving one or more vehicles. More particularly, the present disclosure is directed to systems and methods for collecting and aggregating data associated with accident events, and automatically scheduling provider appointments accordingly.

BACKGROUND

Individuals have been operating and traveling in vehicles as a means of transportation for decades. Unfortunately, vehicles are regularly involved in accident events that may result in or lead to damage, injuries, congestion, or other conditions. Gathering information associated with accident events is difficult and unreliable. Additionally, even when information associated with accident events is able to be gathered, managing the effects of accident events is inefficient and challenging. In particular, individuals associated with the accident events must assess (or have someone else assess) what needs to be addressed (e.g., vehicle damage, bodily injury), which may result in an inaccurate assessment. Further, the individuals must explicitly schedule appointments or services to address the needs.

Accordingly, there is an opportunity for systems and methods to dynamically and automatically collect and aggregate information related to accident events, and dynamically and automatically schedule appointments to address effects of the accident events.

SUMMARY

According to embodiments, a computer-implemented method in an electronic device of managing accident events is provided. The method may include accessing a set of sensor data from a set of sensors associated with a vehicle, determining, from the set of sensor data, that an accident event occurred, the accident event having an associated type, and in response to determining that the accident event occurred, identifying a provider based on the associated type of the accident event, and accessing, via a wireless network connection, an availability of the provider. The method may further include automatically scheduling, via the wireless network connection, an appointment with the provider based on the availability of the provider.

In another embodiment, an electronic device configured to manage accident events is provided. The electronic device may include a transceiver configured to communicate via a wireless network connection, a memory configured to store non-transitory computer executable instructions, and a processor configured to interface with the transceiver and the memory. The processor may be configured to execute the non-transitory computer executable instructions to cause the processor to access a set of sensor data from a set of sensors associated with a vehicle, determine, from the set of sensor data, that an accident event occurred, the accident event having an associated type, and in response to determining that the accident event occurred, identify a provider based on the associated type of the accident event, and access, via the transceiver, an availability of the provider. The processor may further automatically schedule, via the transceiver, an appointment with the provider based on the availability of the provider.

DETAILED DESCRIPTION

Figure 1:
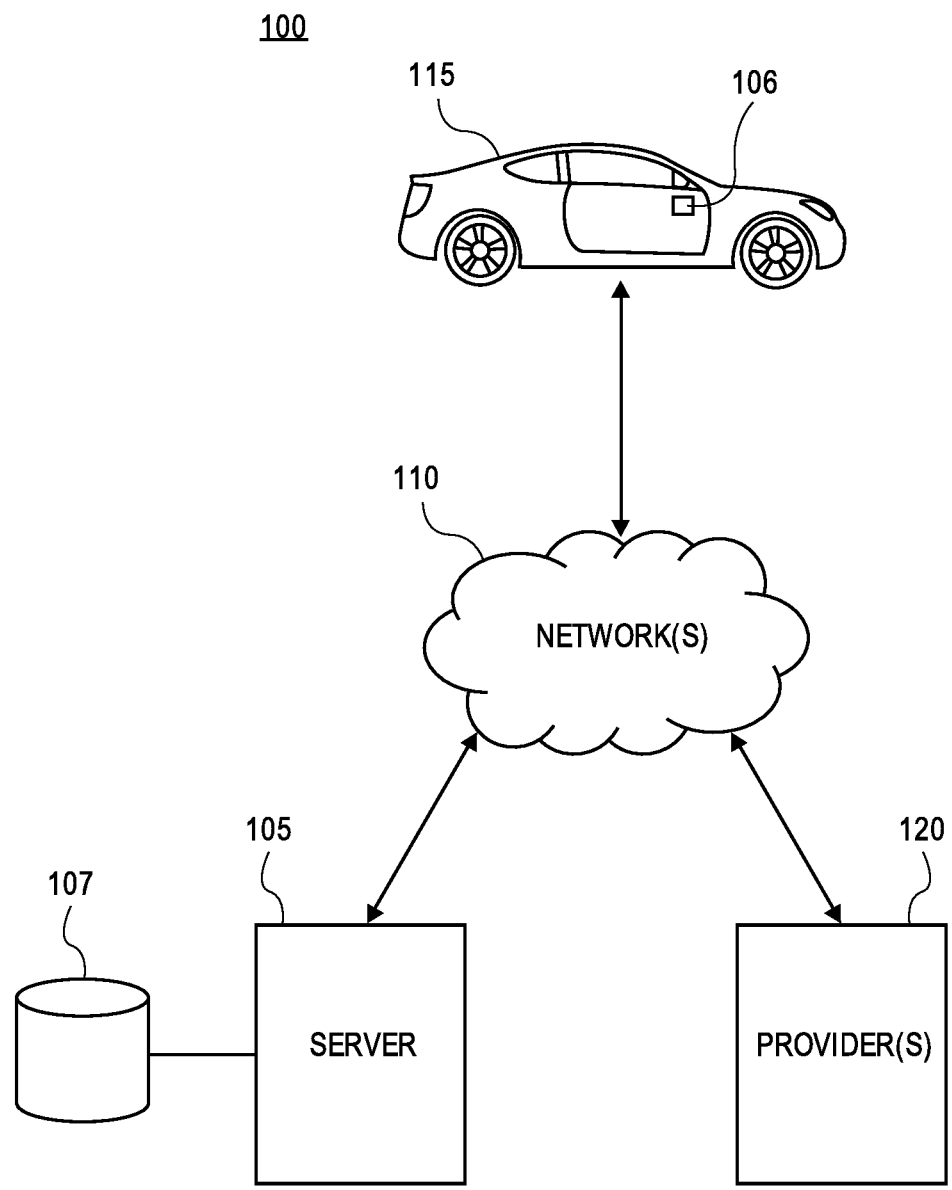
FIG. 1 depicts an overview of an exemplary system of components configured to facilitate various functionalities, in accordance with some embodiments.

The present embodiments may relate to, inter alia, automatically assessing and managing effects that result from accident events. In particular, the present embodiments may automatically detect an occurrence of an accident event as well as determine any damage, injury, or the like that may have incurred as a result of the accident event. Further, the present embodiments may identify one or more service providers capable of attending to the determined effect(s), and automatically schedule an appointment with the service provider(s).

Currently, when an accident event occurs, an individual affected by the accident event (e.g., an individual who suffers an injury and/or whose vehicle is damaged) must wait for a relevant individual (e.g., a mechanic, medical personnel) to assess damage or other effects. Additionally, the affected individual must somehow schedule a medical or service appointment to attend to the effect(s). In other words, there are multiple additional steps that the individual must manually currently undergo or perform when an accident event occurs.

According to certain aspects, the present systems and methods dynamically and automatically facilitate operations in response to accident events. In particular, the systems and methods may retrieve vehicle operation data and, based on the vehicle operation data, determine that an accident event occurred as well as determine any effects resulting from the accident event. The systems and methods may identify a relevant service provider capable of addressing the effects and determine an availability of the relevant service provider. Further, the systems and methods may facilitate scheduling an appointment with the relevant service provider based on the availability and/or other information.

The systems and methods therefore offer numerous benefits. In particular, the systems and methods dynamically and automatically schedule appointments with relevant service providers for individuals affected by accident events and who are in need of the appointments. This negates the need for manual assessment by third parties (e.g., medical personnel and service shops) as well as manual scheduling of appointments by affected individuals. It should be appreciated that other benefits are envisioned.

The systems and methods discussed herein address a business challenge, namely a business challenge related to assessing, managing, and handling the effects of accident events. This is particularly apparent when there are multiple entities and businesses whose services may be needed. In conventional situations, individuals affected by accident events must manually communicate with and schedule needed appointments. In contrast, the systems and methods utilize multiple electronic devices and entities connected via one or more wireless connections to dynamically assess needed services and automatically schedule corresponding appointments using various information.

Therefore, the systems and methods do not merely recite the performance of some business practice known from the pre-Internet world (assessing and managing accident events) along with the requirement to perform it on the Internet. Instead, the systems and methods are necessarily rooted in computer technology in order to overcome a problem specifically airing in computer networks.

Further, it should be appreciated that the systems and methods may include specialized (i.e., non-generic) or dedicated components capable of performing specialized (i.e., non-generic) or dedicated computer functions. In particular, the systems and methods employ various device sensors that are specifically configured to collect certain data. Further, electronic devices interface with the specialized sensors to collect the data and analyze the data.

According to implementations, the systems and methods may support a dynamic, real-time or near-real-time collection, analysis, and communication of any data that may be associated with the assessments. In particular, the systems and methods may dynamically and automatically request and collect operation data from vehicles in real-time or near-real-time, may automatically and dynamically analyze the collected data, may automatically and dynamically identify accident events and damaging relating thereto, and may automatically and dynamically schedule appointments to address the damage.

The term "accident event" as used herein may be used to refer to any accident or incident involving one or more vehicles that collide with each other, and/or make contact with one or more other objects and/or individuals. It should be appreciated that an accident event may also refer to an instance in which a vehicle breaks down, experiences a malfunction, or otherwise ceases to operate. Certain accident events may result in one or more affected or impacted individuals.

FIG. 1 illustrates an overview of a system 100 of components configured to facilitate the systems and methods. It should be appreciated that the system 100 is merely exemplary and that alternative or additional components are envisioned.

As illustrated in FIG. 1, the system 100 depicts a vehicle 115. Although FIG. 1 depicts a single vehicle, it should be appreciated that additional vehicles are envisioned. The vehicle 115 may have at least one associated individual, such as an operator and/or a passenger of the vehicle 115.

The vehicle 115 may have an associated electronic device 106. According to embodiments, the electronic device 106 may be configured with any combination of software and hardware components. In some implementations, the electronic device 106 may be included as part of an on-board diagnostic (OBD) system or any other type of system configured to be installed in the vehicle 115, such as an original equipment manufacturer (OEM) system. In other implementations, the electronic device 106 may belong to the individual associated with the vehicle 115. In particular, the electronic device 106 may be any type of electronic device such as a mobile device (e.g., a smartphone), notebook computer, tablet, phablet, GPS (Global Positioning System) or GPS-enabled device, smart watch, smart glasses, smart bracelet, wearable electronic, PDA (personal digital assistants), pager, computing device configured for wireless communication, and/or the like.

The electronic device 106 may include a set of sensors configured to detect and record various telematics data associated with the vehicle 115. In some implementations, the electronic device 106 may be configured to communicate with (i.e., request, retrieve, or receive data from) a set of sensors disposed within the vehicle 115. According to embodiments, the set of sensors included in the electronic device 106 or otherwise configured to communicate with the electronic device 106 may be of various types. For example, the set of sensors may include a location module (e.g., a global positioning system (GPS) chip), an image sensor, an accelerometer, an ignition sensor, a clock, speedometer, a torque sensor, a throttle position sensor, a compass, a yaw rate sensor, a tilt sensor, a steering angle sensor, a brake sensor, a collision sensor, a damage sensor, and/or other sensors. It should be appreciated that additional sensors are envisioned.

Although not illustrated in FIG. 1, it should be appreciated that the electronic device 106 may be configured to communication with other electronic devices, such as those associated with individual and/or with additional vehicles. In this implementation, the electronic device 106 may be configured to communicate with each other via a network connection such as one or more short range communication protocols such as radio-frequency identification (RFID), Bluetooth®, Bluetooth® low energy (BLE), Infrared Data Association (IrDA), near field communication (NFC), Zig-Bee, other protocols defined under the IEEE 802 standard, and/or other technologies. Generally, the network connection may enable the electronic devices to form a "mesh" network, whereby the electronic devices may automatically connect to one another when in range. When connected, the electronic devices may request, retrieve, access, and/or transmit data thereamongst.

The system 100 may further include a server 105 that may be configured to communicate with the electronic device 106 via one or more networks 110. In certain embodiments, the network(s) 110 may support any type of data communication via any standard or technology (e.g., GSM, CDMA, TDMA, WCDMA, LTE, EDGE, OFDM, GPRS, EV-DO, UWB, Internet, IEEE 802 including Ethernet, WiMAX, Wi-Fi, Bluetooth, and others). The server 105 may be configured to interface with or support a memory or storage 107 capable of storing various data.

Additionally, the system 100 may include one or more providers 120 that may represent any business, corporation, entity, company, individual or group of individuals, and/or the like, that may offer a service capable of addressing effects of accident events. For example, one of the providers 120 may be a tow truck company, another of the providers 120 may be an ambulance service (or a hospital), another of the providers 120 may be an auto body shop. It should be appreciated that many types of providers 120 are envisioned. As illustrated in FIG. 1, the electronic device 106 and the server 105 may be capable of communicating with the provider(s) 120 via the network(s) 110.

According to embodiments, the electronic device 106 may collect sensor/operation data from one or more sensors and determine, from the collected data, that an accident event has occurred, where the accident event may have a particular type. For example, the sensor/operation data may indicate damage to the vehicle 115 (and/or to another vehicle). For further example, the sensor/operation data may indicate that an individual suffered bodily injury, or that there is a high probability that bodily injury occurred.

In response to determining that the accident event has occurred, the electronic device 106 may identify one of the providers 120 that is relevant to the associated type of the accident event (i.e., one of the providers 120 that is capable of addressing effects of the accident event). The electronic device 106 may further access an availability of the identified provider 120, such as a schedule that the provider 120 may avail. The electronic device 106 may automatically schedule an appointment, service, or the like with the provider 120. Accordingly, the provider 120 may address the identified effect(s) of the accident event according to the scheduled appointment without the affected individual having to manually assess the accident event and make an appointment. The electronic device 106 may display an indication of the scheduled appointment for review by the individual associated with the electronic device 106.

Figure 2:
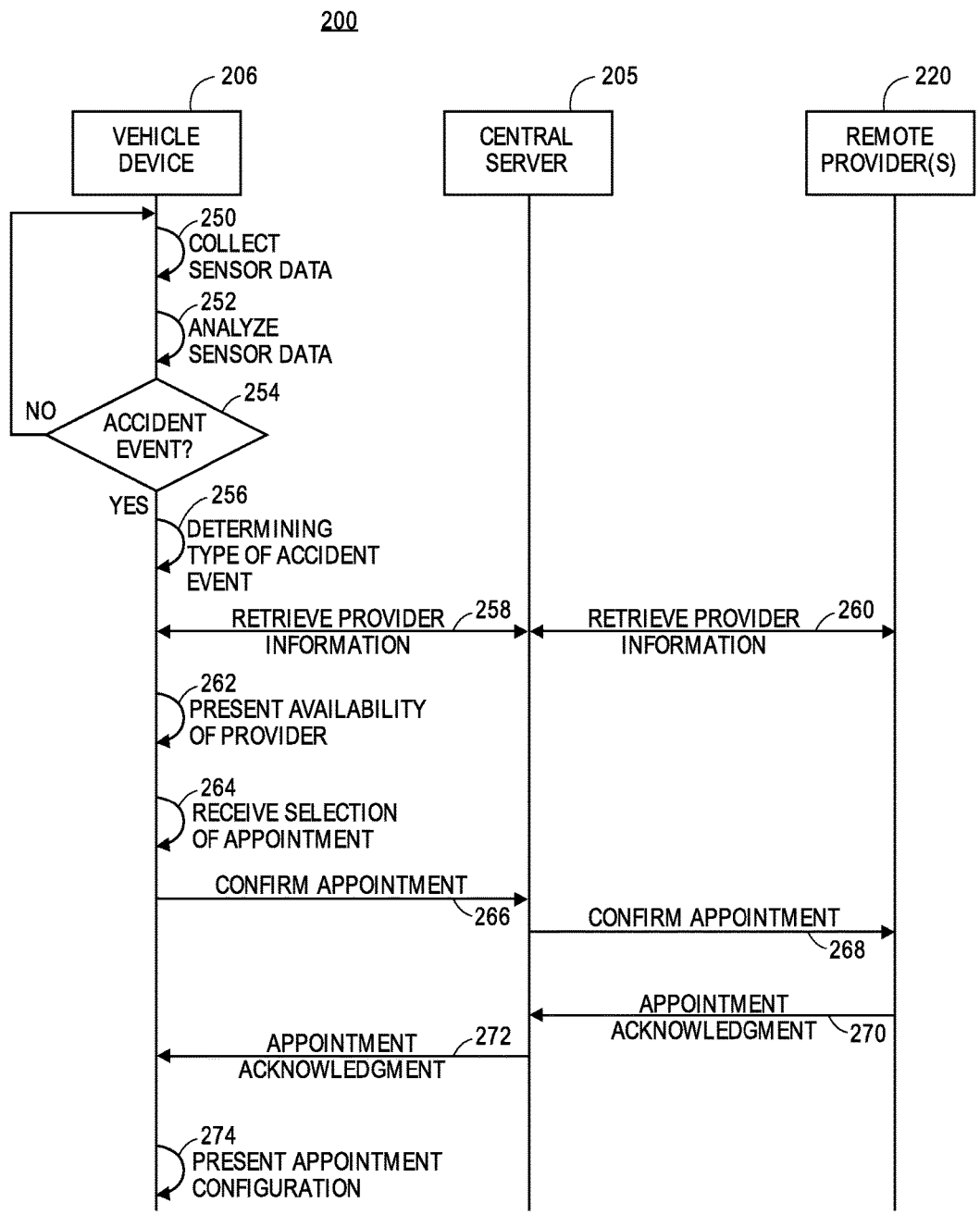
FIG. 2 depicts an exemplary signal diagram associated with assessing and managing accident events, in accordance with some embodiments.

FIG. 2 depicts a signal diagram 200 associated with certain functionalities related to automatically identifying and scheduling provider appointments in response to accident events. The signal diagram 200 includes various components, including a central server 205 (such as the server 105 as discussed with respect to FIG. 1), a vehicle device 206, and at least one remote provider 220. Although FIG. 2 depicts a single vehicle device 206 and a single remote provider 220, it should be appreciated that additional vehicle devices and remote providers are envisioned.

It should be appreciated that the vehicle device 206 may belong to a passenger or operator of the associated vehicle, or may be an on-board device installed within the associated vehicle. According to embodiments, the vehicle device 206 may interface and communicate with the server 205 according to the signal diagram 200. In a particular implementation, the vehicle device 206 may support and execute an application configured to facilitate the communications and functionalities as described herein.

The signal diagram 200 may begin with the vehicle device 206 collecting (250) sensor data. In embodiments, the vehicle device 206 may collect the sensor data continuously (or periodically) and during normal operation of the vehicle, or may collect the sensor data in response to a certain trigger. For example, the vehicle device 206 may collect the sensor data in response to certain operation data meeting or exceeding a threshold value (e.g., vehicle sensors detecting vehicle damage, a strong braking event, etc.). The vehicle device 206 may collect the data from various of the sensors integrated therein, sensors in the vehicle to which the vehicle device 206 may connect, or sensors otherwise associated with the vehicle.

According to embodiments, the sensor data may include data indicative of general vehicle operation including, but not limited to, times and dates when the vehicle is operating (including start time and end time), travel locations or routes (including origin locations and destination locations), distances traveled, speed or velocity, various telematics data (e.g., hard turns, sharp accelerations, hard brakes, etc.), image data, audio data, and/or the like.

The vehicle device 206 may analyze (252) the sensor data. In particular, the vehicle device 206 may analyze the sensor data to determine whether an accident event has occurred. In some implementations, the sensor data may explicitly indicate an accident event. For example, the sensor data may indicate damage to the vehicle. In other implementations, the sensor data may not explicitly indicate an accident event, in which case the vehicle device 206 may determine a certain likelihood of an accident event based on the sensor data, where the vehicle device 206 may deem that an accident event occurred when the certain likelihood at least meets a threshold value. The vehicle device 206 may also identify or determine a time and a location associated with the accident event (i.e., when and where the accident event occurred). Further, in embodiments, the vehicle device 206 may access or retrieve parameters to be used in the determination.

In embodiments, the vehicle device 206 may analyze multiple types and combinations of operation data, where the vehicle device 206 may determine whether the accident event has occurred based on multiple calculated likelihoods, and/or other data. It should be appreciated that the vehicle device 206 may perform or facilitate the determination according to any calculation, technique, algorithm, and/or the like.

The vehicle device 206 may determine (block 254) whether an accident occurred (or whether the determined likelihood of an accident event meets or exceeds a threshold value). If an accident event did not occur ("NO"), processing may return to (250), or may proceed to other functionality.

If an accident event did occur ("YES"), the vehicle device 206 may determine (256) a type of the accident event and/or other characteristics associated with the accident event. In particular, the sensor data may indicate actual or potential damage to the vehicle or to an individual associated with the vehicle (i.e., a passenger). Any vehicle damage may correspond to one or more parts or sections of the vehicle. For example, the sensor damage may indicate that there is damage to the front bumper and the engine of a vehicle. In embodiments, the sensor data may indicate actual damage to the part or section of the vehicle, or the vehicle device 206 may analyze the sensor data to calculate a probability of damage to a particular part or section of the vehicle.

The vehicle device 206 may also estimate, based on the sensor data, whether an individual associated the vehicle may be injured, as well as what type of injury the individual may have sustained. For example, the sensor data may indicate that the air bag deployed, in which case the vehicle device 206 may calculate a likelihood that the driver has a head injury and/or whiplash. For further example, the sensor data may indicate that the driver's side door of the vehicle was impacted, in which case the vehicle device 206 may calculate a likelihood that the driver sustained an injury on his/her left side.

In determining the type of accident event, the vehicle device 206 may also determine a type of provider that may be needed to assist with or address effects of the accident event. In embodiments, certain providers may specialize in attending to different types of damage to either the vehicle or to an individual. For example, if the sensor data indicates that the vehicle is rendered inoperable, then the vehicle device 206 may determine that a tow truck company is a relevant provider. For further example, if the sensor data indicates that the frame or body of the vehicle is damaged, then the vehicle device 206 may determine that an auto body shop is a relevant provider. Additionally, for example, if the vehicle device 206 determines that there is a higher probability of injury to an individual, then the vehicle device 206 may determine that an emergency medical provider (e.g., an ambulance service) is a relevant provider. It should be appreciated that various providers that may assist with or attend to various situations associated with or effects of accident events are envisioned.

The vehicle device 206 may retrieve (258) provider information from the central server 205. In particular, the vehicle device 206 may send a request to the central server 205 that may indicate a type of provider as well as a need for information associated with the type of provider, such as an availability of the provider to assist with the identified damage resulting from the accident event. In embodiments, the request may indicate one or more preferred or available times or dates for appointments. Further, the request may indicate a location of the vehicle device 206, which may be used to identify the provider (i.e., those providers within a vicinity of the location). In these embodiments, the vehicle device 206 may automatically interface with a calendar application to automatically identify the preferred or available times or dates.

In embodiments, the central server 205 may interface (260) with the remote provider(s) 220 to retrieve any requested information. The central server 205 may locally store any provider information (e.g., calendar availability), or may automatically and dynamically retrieve requested information in response to receiving a request from the vehicle device 206. Accordingly, the central server 205 may store or retrieve requested information associated with the remote provider(s) 220, where the requested information may indicate an availability of the remote provider(s) 220 to assist when the determined effect(s) of the accident event. Although not illustrated in FIG. 2, it should be appreciated that the vehicle device 206 may interface directly with the remote provider(s) 220 to request information and receive the requested information.

The vehicle device 206 and/or the central server 205 may prioritize the identification of providers based on various factors. In one embodiment, the vehicle device 206 and/or the central server 205 may identify the distances between the providers and the location of the accident event, and may prioritize any provider(s) that is closer to the accident event than are the other provider(s). In another embodiment, the vehicle device 206 and/or the central server 205 may account for any provider(s) at which the user of the vehicle device 206 has completed a previous appointment or service. For example, the user of the vehicle device 206 may have a preferred or frequented body shop, which may be indicated in a calendar application or similar record.

According to embodiments, the availability of the remote provider(s) 220 may include dates and times when the remote provider(s) 220 is available to attend to or assist with the accident event. For example, if the requested provider is a tow truck service, the retrieved availability information may indicate the a tow truck is immediately available. For further example, if the requested provider is an auto body shop, the retrieved availability information may indicate available appointment dates and times. Additionally, for example, if the requested provider is a hospital or other medical care facility, the retrieved availability information may indicate available appointment dates and times. After accessing or retrieving the provider information, the central server 205 may send the provider information to the vehicle device 206.

The vehicle device 206 may present (262) the provider information, including an indication of the provider as well as an appointment availability of the provider. In embodiments, the vehicle device 206 may present the provider information in a user interface so that a user of the vehicle device 206 may view the provider information. The vehicle device 206 may receive (264), via the user interface, a selection of an appointment. In particular, the user may select to schedule an appointment with the provider at an indicated time and date. In some situations, the appointment may be for immediate assistance (e.g., scheduling a tow truck or calling an ambulance).

After receiving the selection, the vehicle device 206 may send (266) a confirmation to the central server 205 that confirms selection of the appointment. The central server 205 may record the confirmation and forward (268) the confirmation to the remote provider 220. The remote provider 220 may accordingly record that the appointment has been confirmed and may send (270) an acknowledgement of the appointment confirmation to the central server 205. The central server 205 may, in turn, send (272) the acknowledgement of the appointment confirmation to the vehicle device 206. Although not illustrated in FIG. 2, it should be appreciated that the vehicle device 206 may confirm the appointment directly with the remote provider 220 (i.e., without communicating with the central server 205).

The vehicle device 206 may present (274) the appointment confirmation, such as via a user interface. The user of the vehicle device 206 may then be able to know that the appointment was confirmed. In an implementation, the vehicle device 206 may automatically interface with a calendar application to add the appointment to a calendar of the user. Accordingly, at this point in processing, the user of the vehicle device 206 has a confirmed appointment with the remote provider 220.

Although not illustrated in FIG. 2, it should be appreciated that the central server 205 may automatically schedule, for the user of the vehicle device 206, the appointment with the remote provider 220. In an implementation, the central server 205 may automatically schedule the appointment with the remote provider 220 in response to receiving the availability of the remote provider 220, and optionally based on an availability of the user (e.g., such as an availability indicated in a calendar application of the vehicle device 206). In automatically scheduling the appointment, the central server 205 may account for an urgency of the appointment (e.g., immediate assistance needed, or an appointment that may be less urgent such as body work). In this regard, the central server 205 may facilitate identifying the relevant provider 220 and the available appointment, and scheduling the appointment, without needing input from the user of the vehicle device 206.

Figure 3:
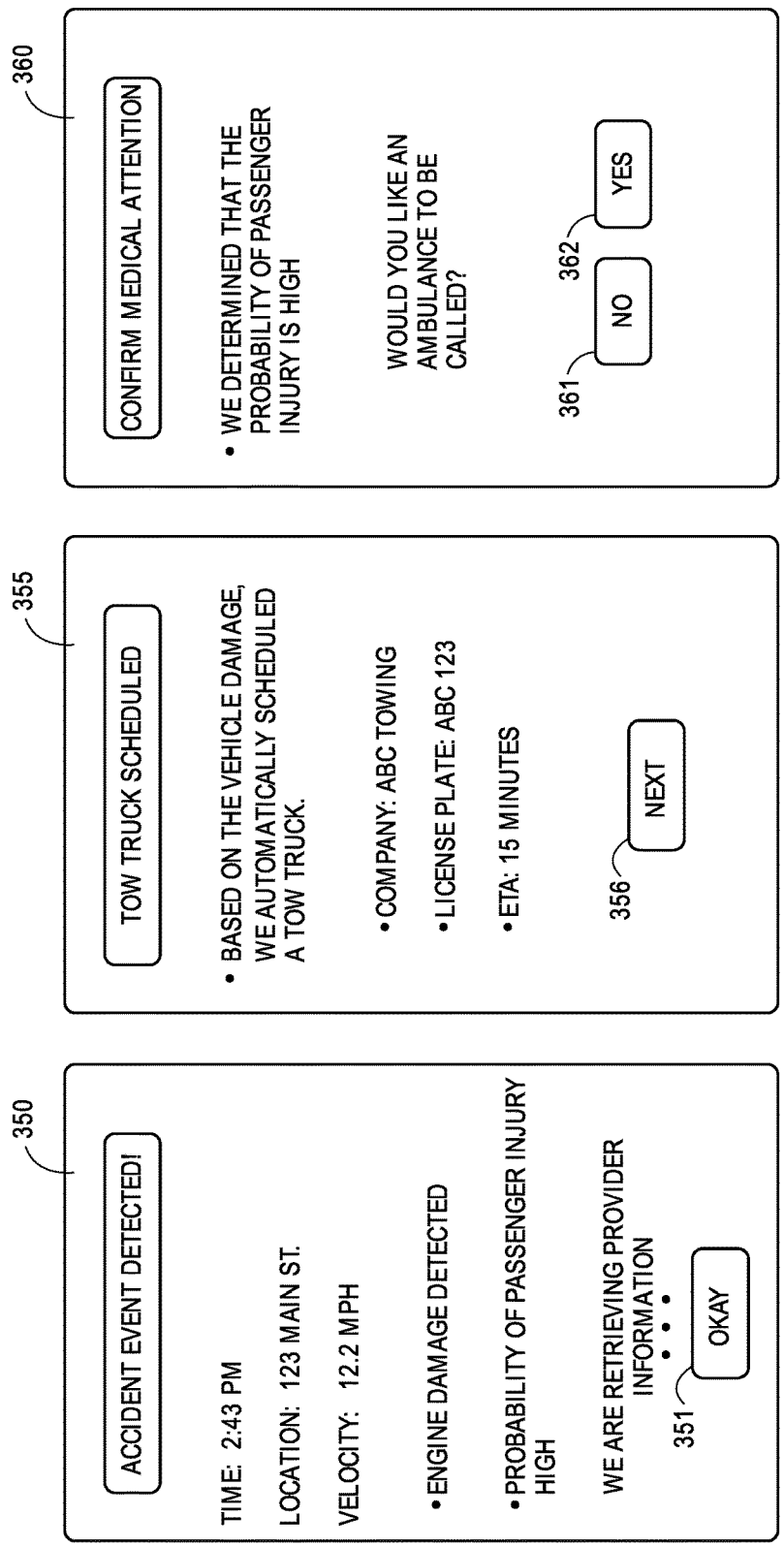
FIGS. 3A-3C depict exemplary user interfaces associated with assessing and managing accident events, in accordance with some embodiments.

FIGS. 3A-3C illustrate exemplary interfaces associated with managing accident events. One or more electronic devices (e.g., a mobile device, such as a smartphone) may be configured to display the interfaces and/or receive selections and inputs via the interfaces, where the electronic device(s) may be associated with an operator or passenger of a vehicle, or may be integrated into the vehicle. For example, a dedicated application that is configured to operate on the electronic device may display the interfaces. It should be appreciated that the interfaces are merely exemplary and that alternative or additional content is envisioned.

FIG. 3A illustrates an interface 350 indicating that an accident event was detected. The interface 350 includes various information associated with the accident event, including a time, location, and velocity (i.e., the velocity of the corresponding vehicle at the time of the accident). The interface 350 further includes an indication that engine damage is detected, and that the probability of passenger injury is high. Additionally, the interface 350 indicates that the electronic device is retrieving information associated with relevant providers that may be able to address the engine damage and/or the passenger injury. The interface 350 includes an okay selection 351 that enables a user to select to dismiss the interface 350.

FIG. 3B illustrates an interface 355 indicating that an appointment for a tow truck was scheduled. The interface 355 includes specific details relating to the appointment, including a tow truck company (as shown: ABC Towing), a license plate of the vehicle to be towed (as shown: ABC123), and an ETA of the tow truck (as shown: 15 minutes). The interface 355 includes an okay selection 356 that enables a user to select to dismiss the interface 355.

FIG. 3C illustrates an interface 360 that enables an individual to select whether medical attention is needed. In particular, the interface 360 indicates that the system determined that the probability of passenger injury is high. Additionally, the interface 360 prompts the individual to select whether an ambulance should be called via a "NO" selection 361 or a "YES" selection 362. In embodiments, if the individual selects the "NO" selection 361, the electronic device may dismiss the interface 360; and if the individual selects the "YES" selection 362, the electronic device may facilitate scheduling or ordering an ambulance, such as from a nearby hospital or medical facility.

Figure 4:
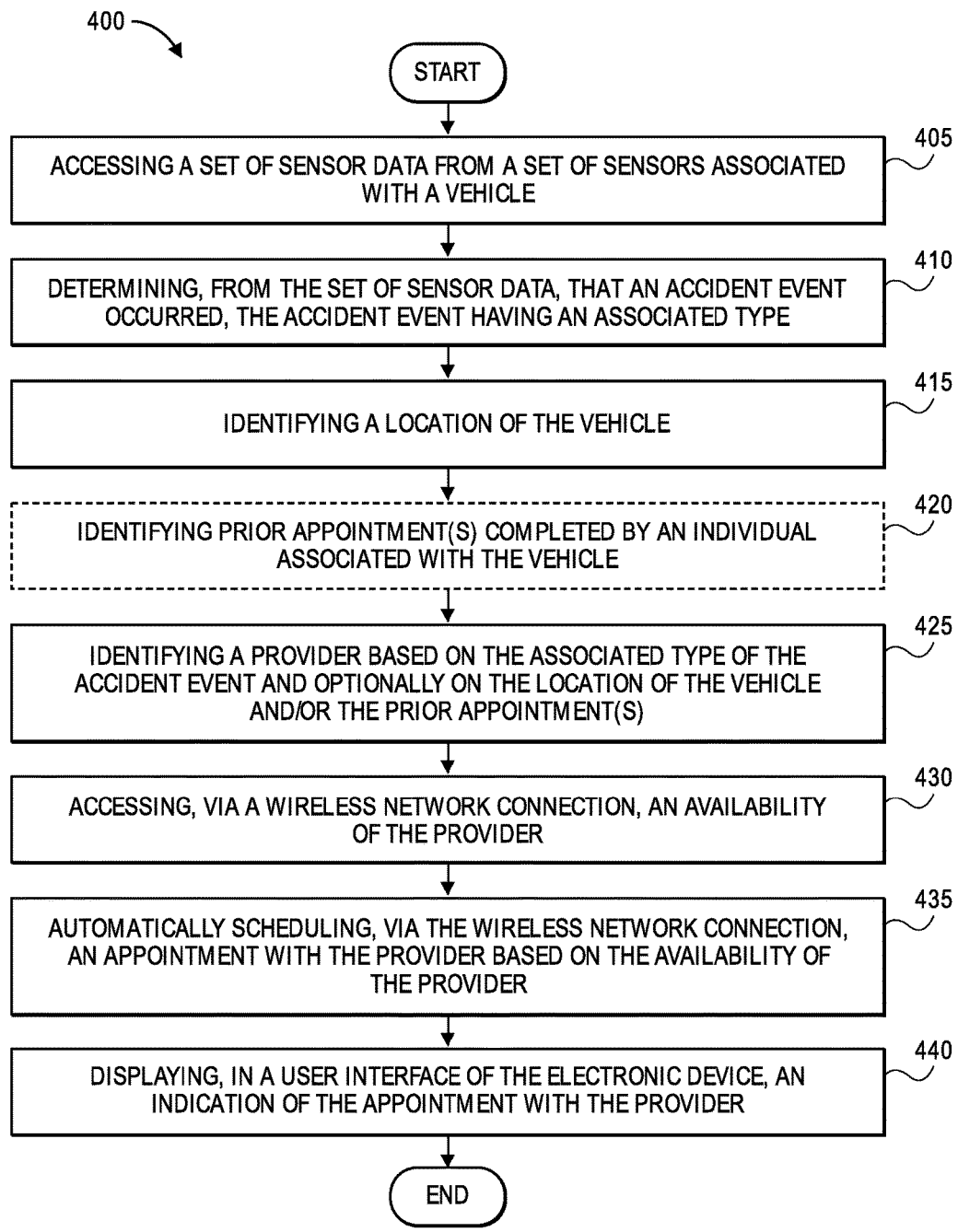
FIG. 4 is a flow diagram associated with assessing and managing accident events, in accordance with some embodiments.

FIG. 4 depicts a block diagram of an exemplary method 400 of managing accident events. The method 400 may be facilitated by an electronic device associated with a vehicle (such as the vehicle device 206) that may communicate with sensors associated with vehicles and with various remote entities and components.

The method 400 may begin with the electronic device accessing (block 405) a set of sensor data from a set of sensors associated with the vehicle. In embodiments, the set of sensors may be incorporated within the electronic and/or may be external to the electronic device (e.g., sensors configured to collect telematics data associated with operation of the vehicle).

The electronic device may determine (block 410), from the set of sensor data, that an accident event occurred. In embodiments, the accident event may have an associated type. In one implementation, the set of sensor data may indicate damage to the vehicle. For example, the set of sensors may include a crash sensor that detects an accident event; or the set of sensors may include an image sensor that captures one or more digital images that depict vehicle damage. In another implementation, the set of sensor data may indicate that an individual associated with the accident event (e.g., a passenger of the vehicle) is injured, or that there is a higher probability of bodily injury. In embodiments, the electronic device may determine that the accident event occurred by determining that the set of sensor data is consistent with stored parameters corresponding to the accident event.

The electronic device may identify (block 415) a location of the vehicle. In embodiments, the electronic device may identify the location via a location module (e.g., a GPS module). The electronic device may optionally identify (block 420) any prior appointments completed by the individual associated with the vehicle. In embodiments, the electronic device may interface with a calendar application installed thereon, or another data record, to automatically identify the prior appointment(s).

The electronic device may identify (block 425) a provider based on the associated type of the accident event and optionally on the location of the vehicle and/or the prior appointment(s). In embodiments, the electronic device may identify the provider based on any combination, weighted or unweighted, of the parameters or inputs. Further, the electronic device may identify multiple applicable providers and may select one of the providers based on a certain metric (e.g., closest to the location of the accident event). The electronic device may access (block 430), via a wireless network connection, an availability of the provider. In particular, the electronic device may wirelessly interface with a calendar system or platform of the provider to retrieve availability information.

The electronic device may automatically schedule (block 435), via the wireless network connection, an appointment with the provider based on the availability of the provider. In an implementation, the electronic device may send, to the provider via the wireless network connection, a request to schedule the appointment, and may receive, from the provider via the wireless network connection, a confirmation of the appointment. In certain embodiments, the electronic device may prompt a user of the electronic device to input or select a desired appointment time according to the availability of the provider. Further, in embodiments, the electronic device may enable the user to confirm an appointment with the provider.

After scheduling the appointment, the electronic device may display (block 440), in a user interface of the electronic device, an indication of the appointment with the provider. Accordingly, the user of the electronic device may effectively and efficiently assess the information and prepare accordingly. In some implementations, the electronic device may access a local schedule or calendar application and add a corresponding entry.

Figure 5:
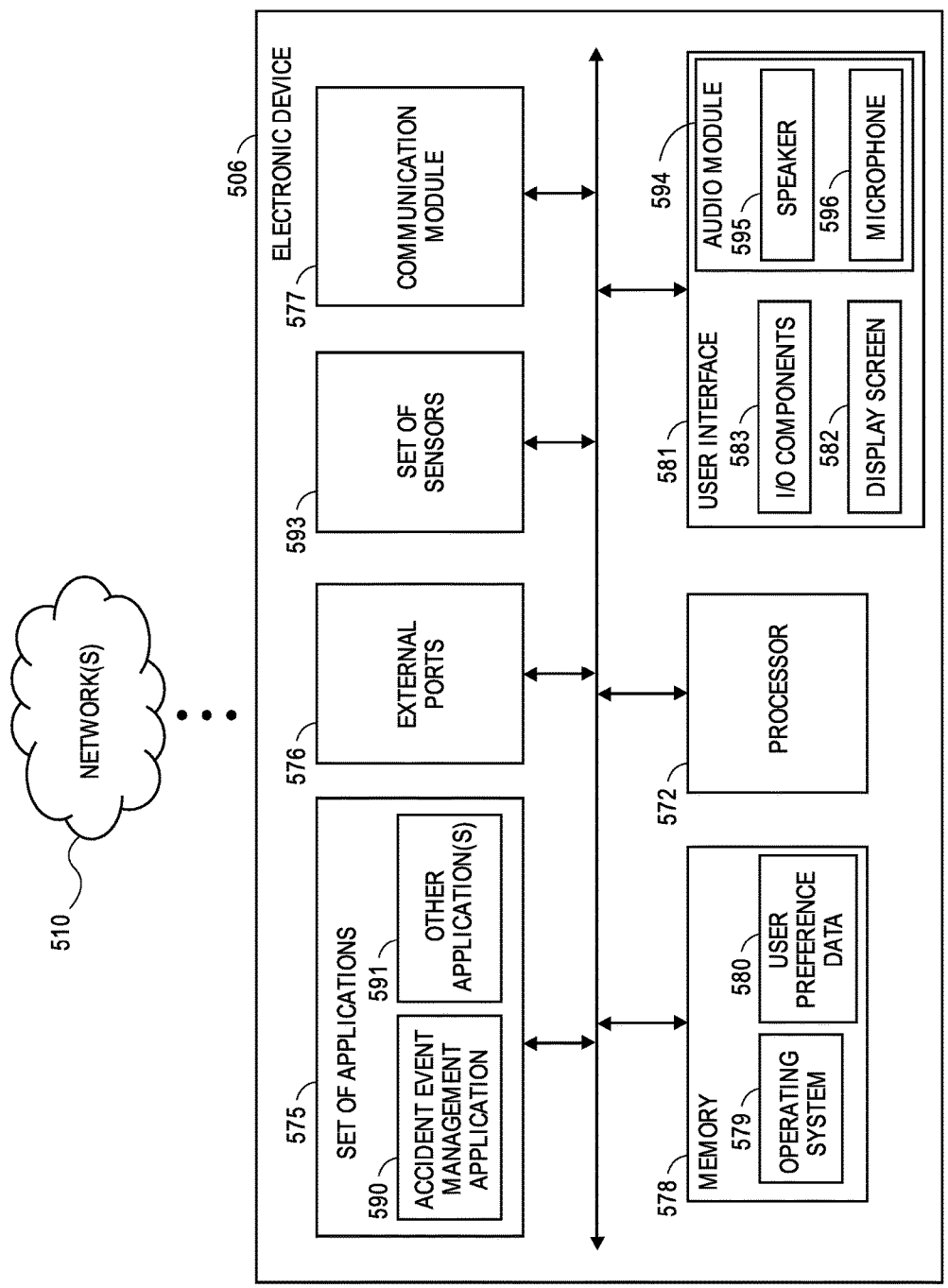
FIG. 5 is a block diagram of an exemplary electronic device, in accordance with some embodiments.

FIG. 5 illustrates a diagram of an exemplary electronic device 506 (such as the vehicle device 206 as discussed with respect to FIG. 2) in which the functionalities as discussed herein may be implemented. It should be appreciated that the electronic device 506 may be configured to be connect to and communicate with various entities, components, and devices, as discussed herein.

The electronic device 506 may include a processor 572 as well as a memory 578. The memory 578 may store an operating system 579 capable of facilitating the functionalities as discussed herein as well as a set of applications 575 (i.e., machine readable instructions). For example, one of the set of applications 575 may be an accident event management application 590 configured to assess and manage accident events. It should be appreciated that one or more other applications 591 are envisioned.

The processor 572 may interface with the memory 578 to execute the operating system 579 and the set of applications 575. According to some embodiments, the memory 578 may also store user preference data 580 that may indicate certain preferences or past appointments with various providers. The memory 578 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others.

The electronic device 506 may further include a communication module 577 configured to communicate data via one or more networks 510. According to some embodiments, the communication module 577 may include one or more transceivers (e.g., WWAN, WLAN, and/or WPAN transceivers) functioning in accordance with IEEE standards, 3GPP standards, or other standards, and configured to receive and transmit data via one or more external ports 576. For example, the communication module 577 may receive, via the network 510, availability information of one or more providers capable of addressing effects of accident events.

The electronic device 506 may further include a user interface 581 configured to present information to a user and/or receive inputs from the user. As shown in FIG. 5, the user interface 581 may include a display screen 582 and I/O components 583 (e.g., ports, capacitive or resistive touch sensitive input panels, keys, buttons, lights, LEDs). According to some embodiments, the user may access the electronic device 506 via the user interface 581 to review information and/or perform other functions. The user interface 581 may also include an audio module 594 that may include a speaker 595 and a microphone 596.

The electronic device 506 may further include a set of sensors 593 such as one or more accelerometers, gyroscopes, imaging sensors, proximity sensors, collision sensors, damage sensors, ultrasonic sensors, and location modules. The set of sensors 593 may also include other types of sensors such as light sensors, infrared sensors, touch sensors, NFC components, and other sensors.

In some embodiments, the electronic device 506 may perform the functionalities as discussed herein as part of a "cloud" network or may otherwise communicate with other hardware or software components within the cloud to send, retrieve, or otherwise analyze data.

In general, a computer program product in accordance with an embodiment may include a computer usable storage medium (e.g., standard random access memory (RAM), an optical disc, a universal serial bus (USB) drive, or the like) having computer-readable program code embodied therein, wherein the computer-readable program code may be adapted to be executed by the processor 572 (e.g., working in connection with the operating system 579) to facilitate the functions as described herein. In this regard, the program code may be implemented in any desired language, and may be implemented as machine code, assembly code, byte code, interpretable source code or the like (e.g., via C, C++, Java, Actionscript, Objective-C, Javascript, CSS, XML). In some embodiments, the computer program product may be part of a cloud network of resources.

Although the following text sets forth a detailed description of numerous different embodiments, it should be understood that the legal scope of the invention may be defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that may be permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that may be temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules may provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it may be communicatively coupled. A further hardware module may then, at a later time, access the memory device to retrieve and process the stored output. Hardware modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment, or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment may be included in at least one embodiment. The appearances of the phrase "in one embodiment" in various places in the specification are not necessarily all referring to the same embodiment.

As used herein, the terms "comprises," "comprising," "may include," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also may include the plural unless it is obvious that it is meant otherwise.

This detailed description is to be construed as examples and does not describe every possible embodiment, as describing every possible embodiment would be impractical, if not impossible. One could implement numerous alternate embodiments, using either current technology or technology developed after the filing date of this application.

What is claimed is:

1. A computer-implemented method in an electronic device of managing accident events, the method comprising:
   accessing a set of sensor data from a set of sensors associated with a vehicle, the set of sensor data at least indicating a location of the vehicle;
   determining, from the set of sensor data, that an accident event occurred;
   in response to determining that the accident event occurred,
      interfacing with an application installed on the electronic device to identify at least one prior appointment completed by an individual associated with the vehicle,
      identifying a provider based on the location of the vehicle, wherein the at least one prior appointment was completed at the provider, and
      accessing, via a wireless network connection, an availability of the provider; and
   automatically scheduling, via the wireless network connection, an appointment with the provider based on the availability of the provider.

2. The computer-implemented method of claim 1, further comprising:
   displaying, in a user interface of the electronic device, an indication of the appointment with the provider.

3. The computer-implemented of claim 1, wherein determining, from the set of sensor data, that the accident event occurred comprises:
   determining, from the set of sensor data, that there is damage to the vehicle;
   and wherein identifying the provider based on the location of the vehicle comprises:
   identifying a vehicle repair provider.

4. The computer-implemented method of claim 1, wherein determining, from the set of sensor data, that the accident event occurred comprises:
   determining, from the set of sensor data, that an individual associated with the vehicle is injured;
   and wherein identifying the provider based on the location of the vehicle comprises:
   identifying a medical provider.

5. The computer-implemented method of claim 1, wherein determining, from the set of sensor data, that the accident event occurred comprises:
   determining, from the set of sensor data, that the accident event occurred, the accident event having an associated type.

6. The computer-implemented method of claim 1, wherein accessing the set of sensor data from the set of sensors associated with the vehicle comprises:
   accessing GPS data from a location module.

7. The computer-implemented method of claim 1, wherein identifying the provider based on the location of the vehicle comprises:
   identifying (i) at least two providers, and (ii) at least two locations respectively associated with the at least two providers; and
   identifying, as the provider, one of the at least two providers whose location is closest to the location of the vehicle.

8. The computer-implemented method of claim 1, wherein automatically scheduling the appointment with the provider comprises:
- connecting to the provider via the wireless network connection;
- sending, to the provider via the wireless network connection, a request to schedule the appointment; and
- receiving, from the provider via the wireless network connection, a confirmation of the appointment.

9. The computer-implemented method of claim 1, wherein the set of sensors are external to the electronic device, and wherein accessing the set of sensor data from the set of sensors associated with the vehicle comprises:
- retrieving the set of sensor data from the set of sensors.

10. The computer-implemented method of claim 1, wherein determining, from the set of sensor data, that the accident event occurred comprises:
- determining that the set of sensor data is consistent with stored parameters corresponding to the accident event.

11. An electronic device configured to manage accident events, comprising:
- a transceiver configured to communicate via a wireless network connection;
- a memory configured to store an application and non-transitory computer executable instructions; and
- a processor configured to interface with the transceiver and the memory, wherein the processor is configured to execute the non-transitory computer executable instructions to cause the processor to:
  - access a set of sensor data from a set of sensors associated with a vehicle, the set of sensor data at least indicating a location of the vehicle,
  - determine, from the set of sensor data, that an accident event occurred,
  - in response to determining that the accident event occurred,
    - interface with the application to identify at least one prior appointment completed by an individual associated with the vehicle,
    - identify a provider based on the location of the vehicle, wherein the at least one prior appointment was completed at the provider, and
    - access, via the transceiver, an availability of the provider, and
  - automatically schedule, via the transceiver, an appointment with the provider based on the availability of the provider.

12. The electronic device of claim 11, further comprising:
a user interface;
wherein the processor is further configured to:
- cause the user interface to display an indication of the appointment with the provider.

13. The electronic device of claim 11, wherein to determine, from the set of sensor data, that the accident event occurred, the processor is configured to:
- determine, from the set of sensor data, that there is damage to the vehicle;

and wherein to identify the provider based on the location of the vehicle, the processor is configured to:
- identify a vehicle repair provider.

14. The electronic device of claim 11, wherein to determine, from the set of sensor data, that the accident event occurred, the processor is configured to:
- determine, from the set of sensor data, that an individual associated with the vehicle is injured;

and wherein to identify the provider based on the location of the vehicle, the processor is configured to:
- identify a medical provider.

15. The electronic device of claim 11, wherein to determine, from the set of sensor data, that the accident event occurred, the processor is configured to:
- determine, from the set of sensor data, that the accident event occurred, the accident event having an associated type.

16. The electronic device of claim 11, further comprising:
a location module;
wherein to access the set of sensor data from the set of sensors associated with the vehicle, the processor is configured to:
- access GPS data from the location module.

17. The electronic device of claim 11, wherein to identify the provider based on the location of the vehicle, the processor is configured to:
- identify (i) at least two providers, and (ii) at least two locations respectively associated with the at least two providers, and
- identify, as the provider, one of the at least two providers whose location is closest to the location of the vehicle.

18. The electronic device of claim 11, wherein to automatically schedule the appointment with the provider, the processor is configured to:
- connect to the provider via the transceiver,
- send, to the provider via the transceiver, a request to schedule the appointment, and
- receive, from the provider via the transceiver, a confirmation of the appointment.

19. The electronic device of claim 11, wherein the set of sensors are external to the electronic device, and wherein to access the set of sensor data from the set of sensors associated with the vehicle, the processor is configured to:
- retrieve the set of sensor data from the set of sensors.

20. The electronic device of claim 11, wherein to determine, from the set of sensor data, that the accident event occurred, the processor is configured to:
- determine that the set of sensor data is consistent with stored parameters corresponding to the accident event.

* * * * *